Figure 1:
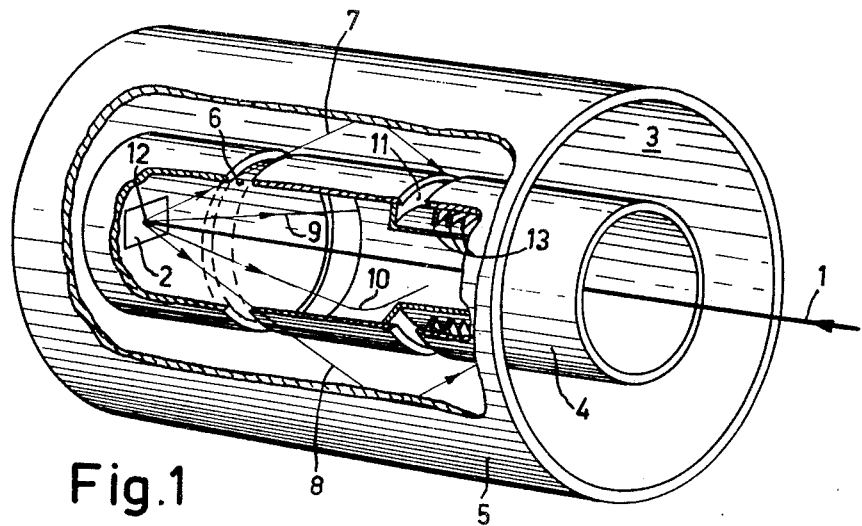

United States Patent [19]

Brongersma et al.

[11] 3,970,849
[45] July 20, 1976

[54] DEVICE FOR MASS ANALYSIS AND STRUCTURE ANALYSIS OF A SURFACE LAYER BY MEANS OF ION SCATTERING

[75] Inventors: Hidde Herman Brongersma; Jacob Walinga, both of Eindhoven, Netherlands

[73] Assignee: U.S. Philips Corporation, New York, N.Y.

[22] Filed: Nov. 19, 1974

[21] Appl. No.: 525,190

[30] Foreign Application Priority Data
Dec. 20, 1973 Netherlands .................. 7317436

[52] U.S. Cl. .............................................. 250/281
[51] Int. Cl.² ........................................ B01D 59/44
[58] Field of Search ............ 250/281, 282, 283, 309

[56] References Cited
UNITED STATES PATENTS

| | | | |
|---|---|---|---|
| 3,480,774 | 11/1969 | Smith................................ | 250/309 |
| 3,621,240 | 11/1971 | Cohen et al. ....................... | 250/282 |
| 3,783,280 | 1/1974 | Watson............................. | 250/282 X |
| 3,786,249 | 1/1974 | Anbar et al........................ | 250/283 |

*Primary Examiner*—Davis L. Willis
*Attorney, Agent, or Firm*—Frank R. Trifari; George B. Berka

[57] ABSTRACT

A device utilizing an energy analyzer having two coaxial cylindrical electrodes, a coaxial ring-shaped detector comprising a large number of individual detector elements to provide information on the atomic structure of the surface layer.

2 Claims, 3 Drawing Figures

DEVICE FOR MASS ANALYSIS AND STRUCTURE ANALYSIS OF A SURFACE LAYER BY MEANS OF ION SCATTERING

The invention relates to a device for mass analysis and structure analysis of a surface layer by means of ion scattering and comprising: means for generating a primary substantially mono-energetic ion beam; a diaphragm aperture for passing a secondary ion beam to be analyzed; and an electrostatic analyzer having a detector for determining the kinetic energy of the ions of the secondary ion beam.

Such a device is known from the U.S. Pat. Spec. No. 3,480,774. In such an ion scattering spectrometer the surface layer to be examined is bombarded with a primary ion beam. The ions of said beam collide with the atoms of the surface layer, which collisions may in certain conditions be considered as elastic. This means that the kinetic energy of an ion after the collision can be calculated by means of the principles of conservation of energy and momentum. If $E_1$ = kinetic energy of an ion prior to the collision
$E_2$ = kinetic energy of an ion after the collision
$m_1$ = mass of the ion
$m_2$ = mass of the atom in the surface layer against which the ion collides
$\gamma = m_2/m_1$
$\theta$ = the angle of scattering, that is the angle between the velocity vectors of the ion prior to and after the collision, then it holds, if $\gamma > 1$, as is known that $$E_2 = [\{\cos\theta + (\gamma^2 - \sin^2\theta)^{1/2}\}/(1+\gamma)]^2 E_1$$

From this it follows that $m_2$ can be determined by measuring $E_2$ if $m_1$, $E_1$ and $\theta$ are known and if it may be assumed that only single collisions take place. In an ion scattering spectrometer this is done as follows. A beam of ions, usually rare gas ions, of known mass $m_1$ and known energy $E_1$ is directed on the surface layer to be examined. A diaphragm is arranged so that the direction of scattered ions which pass through the gap enclose a known angle $\theta$ with the direction of the primary beam. The energy of the passed ions is measured in an energy analyzer. With a given voltage at the electrodes of the energy analyzer, only scattered ions of a given energy $E_2$ can pass through the analyzer. Hence said energy, given $m_1$, $E_1$ and $\theta$ is characteristic of the mass $m_2$ of atoms in the surface layer which are hit by the primary beam. By varying the voltage at the electrodes of the analyzer, a spectrum can be obtained of the types of atoms occurring in the surface layer. With given voltages at the analyzer, a peak occurs in the signal which the detector supplies. The value of the peak is a measure of the relative quantity of the relevant atoms and the voltage at the analyzer belonging to the peak is a measure of the mass of the relevant atoms.

It is obvious that the angle $\theta$ must be accurately determined and the aperture in the diaphragm should hence be so small that only few scattered ions are passed. In practice, $\theta$ should be determined to an accuracy of 1° to 2° by the diaphragm which has for its result for the known device that only scattered ions within a space angle of 2° × 2° can be accepted so that only a very small signal is obtained.

An energy analyzer having two coaxial cylindrical electrodes is known from the article "Zur Energieverteilung der von Protonen in Gasen ausgelösten Sekundärelektronen" in "Zeitschrift für Physik", Volume 147, pp. 228–240, 1957. Such an analyzer has the advantage that the paths of the scattered ions which enclose a given angle with the axis of the analyzer, with which axis the axis of the primary beam coincides, lie on a conical surface. By using an annular diaphragm having a gap which is 2° wide and has a circumference of 360°, much more ions are accepted by the analyzer than by the analyzer which is used in the device described in the U.S. Pat. No. 3,480,774. However, such an analyzer could not be used so far in an ion scattering spectrometer because the primary ion beam is to extend along the axis of the analyzer and hence either the surface layer to be examined or the detector form an obstruction for the primary ion beam. A solution to this problem is given in the U.S. patent application Ser. No. 577,069 in which it is described how the primary ion beam can be deflected along the axis of the analyzer via apertures in the cylindrical electrodes of the analyzer. Another solution is given in the U.S. patent application Ser. No. 466,220 in which it is described that the detector is annular and the primary ion beam is directed through the aperture in the centre of the detector. However, with the annular detector described in said application, only mass analysis, that is the determination of the type of the atoms in the surface layer, but no structure analysis, that is the determination of the mutual position of the atoms in the surface is possible.

It is the object of the invention to provide an ion scattering spectrometer with which in addition to mass analysis, structure analysis of the surface layer is also possible.

According to the invention, a device of the type mentioned in the first paragraph is characterized in that the electrostatic analyzer comprises two substantially cylindrical coaxial electrodes, that the said diaphragm aperture has a substantially annular shape and is coaxial with the analyzer, and that the detector comprises a large number of individual detector elements which are arranged in a ring which is substantially coaxial with the analyzer.

A device according to the invention preferably has a detector which comprises: at least one annular, electron-multiplying channel plate and a ring of individual electrodes which are arranged on the output side of the channel plate. Ions which are incident on the input side of the channel plate liberate secondary electrons there, the number of which is multiplied by the channel plate and which land on the said electrodes.

Figure 2:
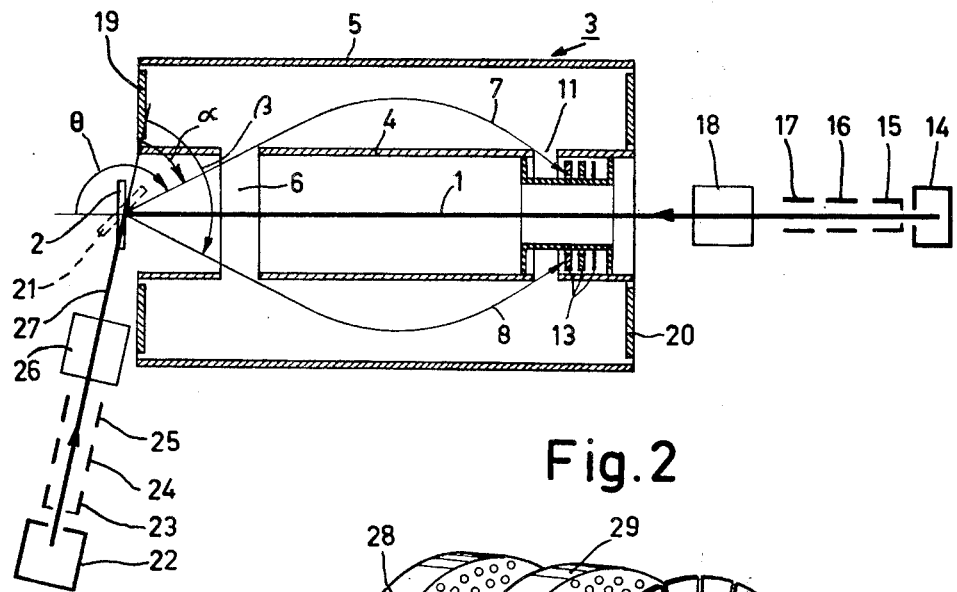
Figure 3:
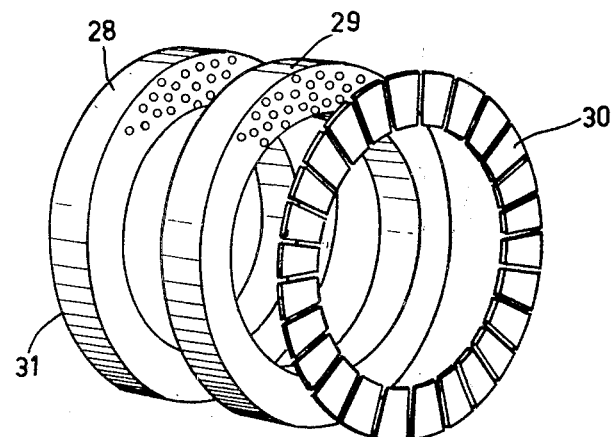

The invention will be described in greater detail with reference to the accompanying drawing, of which:

FIG. 1 is a perspective drawing, partly broken away, of a cylindrical analyzer for a device according to the invention, FIG. 2 is a diagrammatic sectional view of a modified device according to the invention, and FIG. 3 shows a detector for a device according to the invention.

Referring now to FIG. 1, a primary substantially mono-energetic ion beam 1 impinges upon a target 2 with an energy $E_1$ of, for example, a few hundred eV. The ions should be selected for mass, charge and energy, which may be carried out with means which are known from the prior art and need not be further explained. Rare gas ions, for example helium ions or neon ions, are preferably used. An advantage of said ions is their large electron affinity (ionization energy of the atom). With an angle of scatter which exceeds 90°, there is a fair chance that their charge is neutralized in the collision. Although this results in a small number of scattered ions, it also minimizes the possibility of detection of multiple collisions which spoil the measurement upon mass analysis. It is just a property of a device according to the invention that sufficient signal is still generated by the detector also in the case of a small number of scattered ions.

The axis of the primary ion beam 1 coincides with the axis of an energy analyzer 3. The energy analyzer 3 comprises two coaxial cylindrical electrodes 4 and 5. The ions of the beam 1 impact against atoms in the surface layer of the target 2 and are scattered. They lose a given quantity of energy which depends upon the angle of scatter and the mass $M_2$ of the atom in the surface layer. The energy analyzer 3 measures said energy loss for one fixed angle $\theta$ (FIG. 2) which exceeds 90°. So in this case we have to do with back scattering. The angle $\theta$ may be, for example, 141° so that the ions accepted by the energy analyzer describe paths over the surface of a cone having an apical angle of 78°. The angle $\theta$ is determined by the position of the diaphragm aperture 6 in the cylindrical electrode 4 relative to the target 2. In the radial electric field between the electrodes 4 and 5 the scattered ions describe quasi-parabolic paths a few of which are denoted by 7, 8, 9 and 10 and can pass through the second diaphragm aperture 11 only at a given potential difference between the electrodes 4 and 5 which is a measure of their energy. The energy $E_2$ analyzer 3 focuses ion paths which start in the point 12 on the target 2 in an annular focus behind the diaphragm aperture 11. At this site an annular detector 13 is arranged to detect the scattered ions. Said annular detector 13 which will be described in greater detail with reference to FIG. 3, surrounds the primary ion beam so that same can reach the target 2 without hindrance.

FIG. 2 is a sectional view of a modified device of FIG. 1 shown in a plane through the axis of the primary ion beam 1. The beam 1 can be generated by an ion source 14, extracted by an extraction electrode 15, focused by focusing electrodes 16 and 17 and selected for mass $m_1$ by a mass filter 18 and then impinges upon the target 2. Alternately, a primary ion beam 27 can be generated by an ion source 22 located near the target end of the analyzer 3, extracted by an extraction electrode 23, focused by focusing electrodes 24 and 25 and be selected for mass by a mass filter 26 and then impinges upon the target in another position 21 with respect to the diaphragm aperture 6. The energy analyzer 3 has the same reference numerals as in FIG. 1.

The angle of scatter of the ions which are accepted by the energy analyzer 3 is determined by the relative angular position of diaphragm aperture 6 in the inner electrode 4 and the target 2. Said angle of scatter is a fixed angle $\theta$ for the ions of the beam 1 whereas for the beam 27 it lies between the angles $\alpha$ and $\beta$ as shown in FIG. 2. In principle, only one of the beams 1 and 27 need be generated, dependent upon the kind of experiment. Only information relating to one angle of scatter is obtained by means of the beam 1, so that only the mass $M_2$ of the atoms in the surface layer is analysed. Information about a large number of angles of scatter is obtained simultaneously by means of the beam 27. This is carried out by using a ring of detectors which divides the region between the angles $\alpha$ and $\beta$ into a large number, for example 120, of segments each with an angle resolving power of approximately 3°. Said ring of detectors is shown in FIG. 3. From information obtained simultaneously on a large number of angles of scatter, important conclusions can be drawn on the structure of the surface layer. With the angles of scatter which are obtained with the beam 27 and which are smaller than 90°, there actually exists a fair chance of multiple collisions. This is the case in particular when the beam consists of heavy rare gas ions. Certain assumptions can be made on such collisions, for example, that the collision is two-fold and that the masses of the atoms in the layer to be examined with which the collision takes place are known. Of course, the results of a mass analysis having taken place previously are used. By using the already stated collision formula twice and making use of the measured total angle of scatter, the two angles of scatter of the individual collisions can be calculated. From this an insight in the atomic structure of the layer can be gained.

The detector shown in FIG. 3 which is denoted by 13 in FIGS. 1 and 2 consists of a ring of detector elements. The detector comprises a first annular channel plate 28, a second annular channel plate 29 and a ring of electrodes 30 which are arranged coaxially with the energy analyzer 3 behind the diaphragm aperture 11. Channel plates are known per se and consist of sheet of a few millimeters thickness which is provided with an electrode on both surfaces. In plate has a very large number of fine channels which open into both surfaces of the plate and the wall of which has secondary emission with a secondary emission factor exceeding 1. A voltage difference is applied between the electrodes on both surfaces, so that in the channel a voltage gradient prevails in such manner that electrons are accelerated from the input side of the plate to the output side. Ions accepted by the analyzer are post-accelerated to an energy of a few keV after passing through the diaphragm aperture 11 by applying a voltage difference between the electrode 4 and the electrode on the input side 31 of the channel plate 28. The ions liberate secondary electrons on the input side 31 of the channel plate 28 and the local secondary flow of electrons is intensified in the channels by repeated collisions of the electrons with the wall of the channels so that on the output side of the plate an amplified electron pulse is available per accepted ion. The number of pulses per second is proportional to the current strength of the particles to be analyzed on the input side.

The detector 13 comprises two channel plates 28 and 29 to increase the amplification. The channels in the plates 28 and 29 enclose a small angle with each other so as to stop ions which are formed in the channel and which may cause all kinds of undesired effects. The amplified secondary electron pulse which is available at the output side of the plate 29 is received by the ring of electrodes 30. The electrodes of the ring 30 are connected to a voltage which is positive with respect to the voltage on the electrode at the output side of the plate 29. The number of pulses per second which an electrode of the ring 30 supplies is a measure of the number of scattered ions of the beam 27 for a given angle of scatter. So information can simultaneously be obtained on a large number of angles of scatter with which structure analysis can be performed. In a successive measurement for a large number of angles of scatter this would not be possible because the structure of the surface layer to be analyzed would vary during the measurement.

Upon performing measurements with the beam 1, the electrodes of the ring can be interconnected because the angle θ then is the same for all the scattered ions which are accepted by the analyzer.

For a good operation of the energy analyzer 3 shown in FIGS. 1 and 2, the electric field between the electrodes 4 and 5 should be equal everywhere to the field between two infinitely long coaxial cylinders. Since in practice the cylinders have a restricted length, electrodes have to be provided so as to establish the peripheral conditions for the field and, if desired, to correct the field slightly. For that purpose, the cylinders 4 and 5 are closed by means of the plates 19 and 20 which are not shown in FIG. 1 for clarity. The plates 19 and 20 are at an average potential between that of the cylinders 4 and 5. It is also possible to divide the plates 19 and 20 into several electrodes with different potentials so as to obtain a better approach of the required electric field or to adapt the shape of the plates as readily as possible to the required field configuration. The plates may also be made of a material having a large electric resistance and be connected to the cylinders 4 and 5 so as to obtain a uniformly varying potential.

It is to be noted that in the derivation of the collision formula used the movement of the atoms of the target has been neglected. Said movement gives a widening of the peak in the signal of the detector. Cooling of the target may hence be of advantage so as to be able to distinguish peaks of the spectrum which are situated immediately beside each other.

Near the target a low energy electron gun or a filament may be arranged so as to ensure space charge compensation in known manner. It is furthermore possible to peel the target slowly layer by layer with the ion beam, while measurements are performed by means of the beam 27, or conversely, so as to be able to analyze also deeper located layers in this manner.

In the device shown in the drawing, the inside diameter of the electrode 5 is 125 mm and the outside diameter of the electrode 4 is 50 mm. The distance between the point 12 on the target 2 and the centre of the annular detector 13 is 90 mm. The angle θ is 141°. The electrode 4 is connected to earth in connection with the transport of the primary ion beam 1. For selecting singly charged ions with an energy of V electron volt, the potential of the electrode 5 (relative to the electrode 4) should then be V volt.

The ion source 14 supplies an ion current of the order of magnitude of a few nano-amperes to a few micro-amperes with an energy which is adjustable from a few tens of volts to a few kilovolts. As already noted, rather high requirements are imposed upon the energy spreading of the ions which emerge from the ion source. In practice it should be between 0.1 and 3.0 eV, which is possible with ion sources which are known from the prior art.

The mass filters 18 and 26 preferably consist of the known Wien filter. In said filter the beam is subjected to the influence of an electric and a magnetic field the directions of which are perpendicular to each other and to the axis of the beam. This has for its result that only ions of the substantially monoenergetic ion beam having one given mass are not deflected and can pass through the filter. The other ions are deflected indeed and intercepted by means of a diaphragm at some distance from the mass filter.

The part of the electrode 4 between the target 2 and the diaphragm aperture 6 preferably comprises a number of radial partitions not shown. This prevents that ions are accepted which have a certain angular velocity with respect to the axis of the analyzer, which, naturally, would reduce the angle resolving power of the analyzer which may be 3° with a ring of, for example, 120 electrodes.

Between the diaphragm aperture 11 and the input side 31 of the channel plate 28, preferably not only post-acceleration but also mass separation takes place so as to prevent ions which are liberated from the target itself and which might happen to be accepted by the analyzer from disturbing the measurement. Said mass separation may be carried out with two sets of annular grids between the diaphragm aperture 11 and the channel plate 28 which are connected to a high frequency voltage. Said grids then constitute a high frequency mass spectrometer as described in the Canadian Journal of Physics, 1952, volume 30, pp. 1–9. When the choice of the frequency and the voltage is correct, only the desired ions are passed.

Since scattering with angles of scatter exceeding 90° (beam 1) is restricted to surface layer atoms which are heavier than the ions of the beam, the element hydrogen cannot be detected with the beam 1. This can be done indeed with angles of scatter smaller than 90° so that the element hydrogen which is lighter than the lightest rare gas ion can also be detected with the beam 27.

What is claimed is:

1. A device for mass analysis and structure analysis of a surface layer of a target, comprising: means for generating a primary, substantially monoenergetic ion beam, means for directing said beam to said target; an energy analyzer including two substantially coaxial electrodes for producing an electrostatic radial field therebetween, the center axis of said electrodes coinciding with the intersection of said primary beam and said target, the inner electrode having a substantially annular aperture the position of which relative to said intersection determines the angles of scatter whereas the size of which together with said radial field determines the focal area for the scattered secondary ion beam; and means for detecting the secondary ion beam, said detecting means including a plurality of ion detectors arranged around said center axis in said focal area to detect a plurality of angles of scatter of the secondary ion beam.

2. A device as claimed in claim 1 wherein the detecting means comprises: at least one annular, electron-multiplying channel plate and a ring of individual electrodes which are arranged on the output side of the channel plate.

* * * * *

UNITED STATES PATENT AND TRADEMARK OFFICE
CERTIFICATE OF CORRECTION

PATENT NO. : 3,970,849
DATED : July 20, 1976
INVENTOR(S) : HIDDE H. BRONGERSMA ET AL It is certified that error appears in the above-identified patent and that said Letters Patent are hereby corrected as shown below:

Column 2, line 27, after "surface" insert --layer--;

Column 3, line 29, delete "$E_2$" and after "energy" (first occurance) insert --$E_2$--.

Signed and Sealed this

Twenty-first Day of September 1976

[SEAL]

Attest:

RUTH C. MASON
*Attesting Officer*

C. MARSHALL DANN
*Commissioner of Patents and Trademarks*